(12) United States Patent
Chen

(10) Patent No.: US 7,331,065 B1
(45) Date of Patent: Feb. 19, 2008

(54) DEVICE TO AID IN SHIFTING A PAIR OF GOGGLES

(76) Inventor: Chih-Ming Chen, No. 19, Alley 4, Lane 234, Sec. 5, Her Wei Road, Tainan City (TW)

( * ) Notice: Subject to any disclaimer, the term of this patent is extended or adjusted under 35 U.S.C. 154(b) by 0 days.

(21) Appl. No.: 11/492,866

(22) Filed: Jul. 26, 2006

(51) Int. Cl.
*A61F 9/02* (2006.01)

(52) U.S. Cl. ........................................ 2/448

(58) Field of Classification Search ............. 2/448–452
See application file for complete search history.

(56) References Cited

U.S. PATENT DOCUMENTS 5,642,178 A * 6/1997 Leonardi et al. ............ 351/111
5,666,663 A * 9/1997 Bolle ............................. 2/10
5,734,995 A * 4/1998 Chiang .......................... 2/428
5,809,580 A * 9/1998 Arnette .......................... 2/426
6,859,947 B2 * 3/2005 Lee ................................ 2/428

* cited by examiner

*Primary Examiner*—Katherine Moran
(74) *Attorney, Agent, or Firm*—Rosenberg, Klein & Lee

(57) ABSTRACT

A device to aid in shifting a pair of goggles is disclosed. The device comprises two belt-connecting units attached to two lateral edges of a goggles frame, respectively. Each of the belt-connecting units is composed of abutted rigid member and flexible member, which are made of different materials. The rigid members are attached to the lateral edges of the goggles frame, respectively. Each of the flexible members has an elastic linkage part extending therefrom for connection with an elastic belt. As a result, the elastic linkage parts are flexibly deformable so as to provide convenience and comfort in shifting the goggles worn on the user's head.

3 Claims, 5 Drawing Sheets

DEVICE TO AID IN SHIFTING A PAIR OF GOGGLES

FIELD OF THE INVENTION

The present invention relates to a pair of goggles, and more particularly to a device attached between an elastic belt and a goggles frame of the goggles.

BACKGROUND OF THE INVENTION

As shown in FIGS. 1 and 2, a pair of presently commercial goggles such as snow goggles generally comprises a goggles frame 1 having a pair of lens 11 embedded thereon, wherein the goggles frame 1 has two through holes 12 formed respectively on both sides so as to allow an elastic belt 2 to pass therethrough so that the elastic belt 2 can be sleeved onto the head. In addition, the inner flanges of the goggles frame 1 can be placed on the regions surrounding the eyes to guard the eyes and protect the eyes against the wind.

Furthermore, when the wearer who wears the goggles for action wants to take a rest or release himself/herself from the contraction force, he/she usually shifts the goggles frame 1 to a headgear or helmet instead of removing it directly. However, the elastic belt 2, which is tightly placed on the wearer's head, is made of a soft material that it has no proper point to which a force can be applied. Accordingly, in order to shift the goggles frame 1 and sleeve it onto the headgear or helmet, the wearer usually grips the goggles frame 1 by fingers and pulls it away from the face followed by shifting it upwardly. However, the motion of outward pulling the goggles frame 1 causes the elastic belt 2 to fasten up the wearer's head more tightly, resulting in the increase of contraction force. Besides, the elastic belt 2, which sways upward by an angle by the upward movement of the goggles frame 1, also scrapes or pulls the hair or skin especially on both sides of the wearer's head, causing the discomfort, such as pain.

SUMMARY OF THE INVENTION

In view of the above-mentioned conventional drawbacks, a major object of the present invention is to disclose a device to aid in shifting a pair of goggles. The device comprises two belt-connecting units attached to two lateral edges of a goggles frame, respectively, wherein each of the belt-connecting units is composed of a rigid member and a flexible member so that the belt-connecting units are outwardly bendable and upward/downward swayable. The elastic linkage parts are flexibly deformable so as to provide convenience and comfort in shifting the goggles worn on the user's head.

In order to achieve the object of the present invention, a device to aid in shifting a pair of goggles is comprised of two belt-connecting units attached respectively to two lateral edges of a goggles frame. Each of the belt-connecting units is composed of a rigid member and a flexible member, which are abutted to each other and made of different materials. The rigid members are attached to the lateral edges of the goggles frame, respectively. Each of the flexible members has an elastic linkage part extending therefrom for connection with an elastic belt. As a result, the elastic linkage parts are flexibly deformable so as to provide convenience and comfort in shifting the goggles worn on the user's head.

DETAILED DESCRIPTION OF THE PREFERRED EMBODIMENT

The description taken with the drawings make the structures, features, and embodiments of the present invention apparent to those skilled in the art how the present invention may be embodied in practice.

Figure 1:
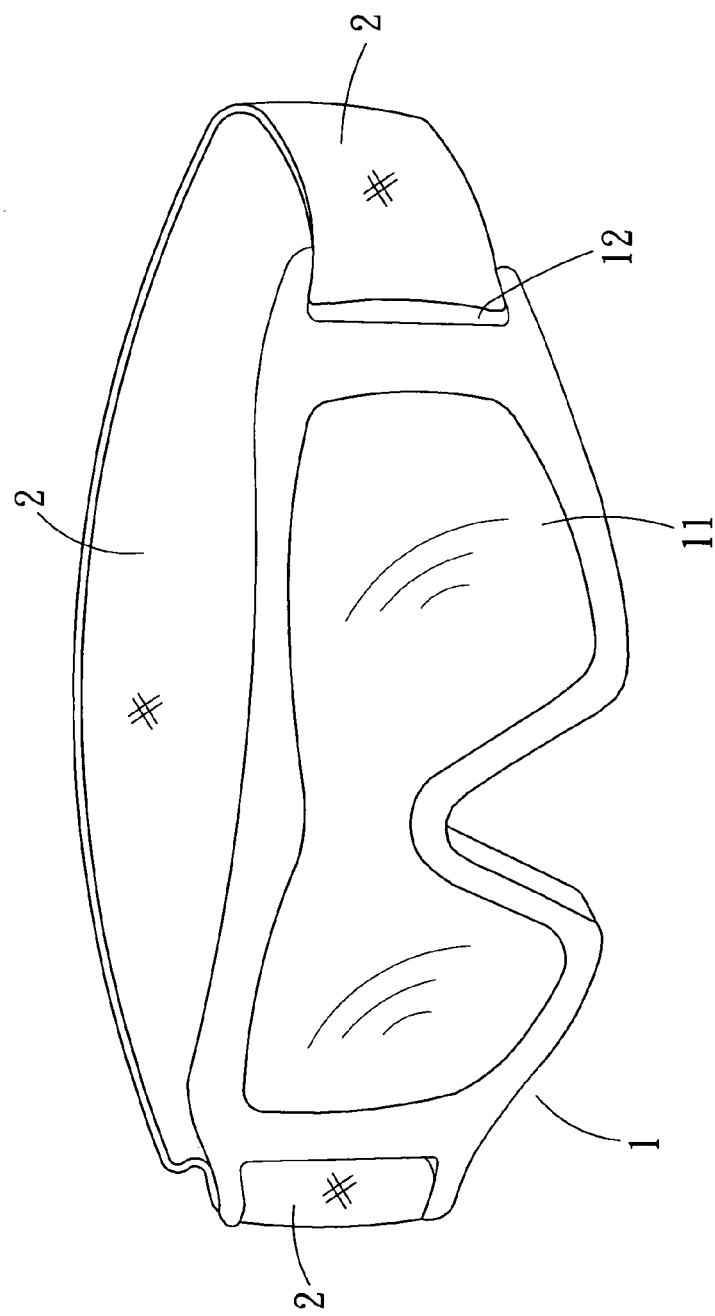
FIG. 1 is an elevational diagram of the conventional structure.
Figure 2:
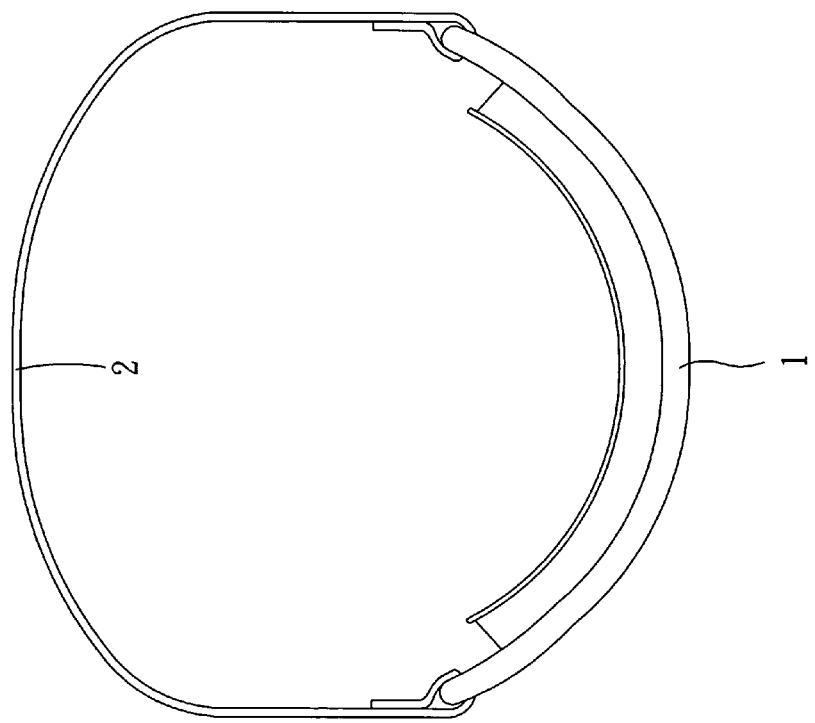
FIG. 2 is a top view showing the conventional structure.
Figure 3:
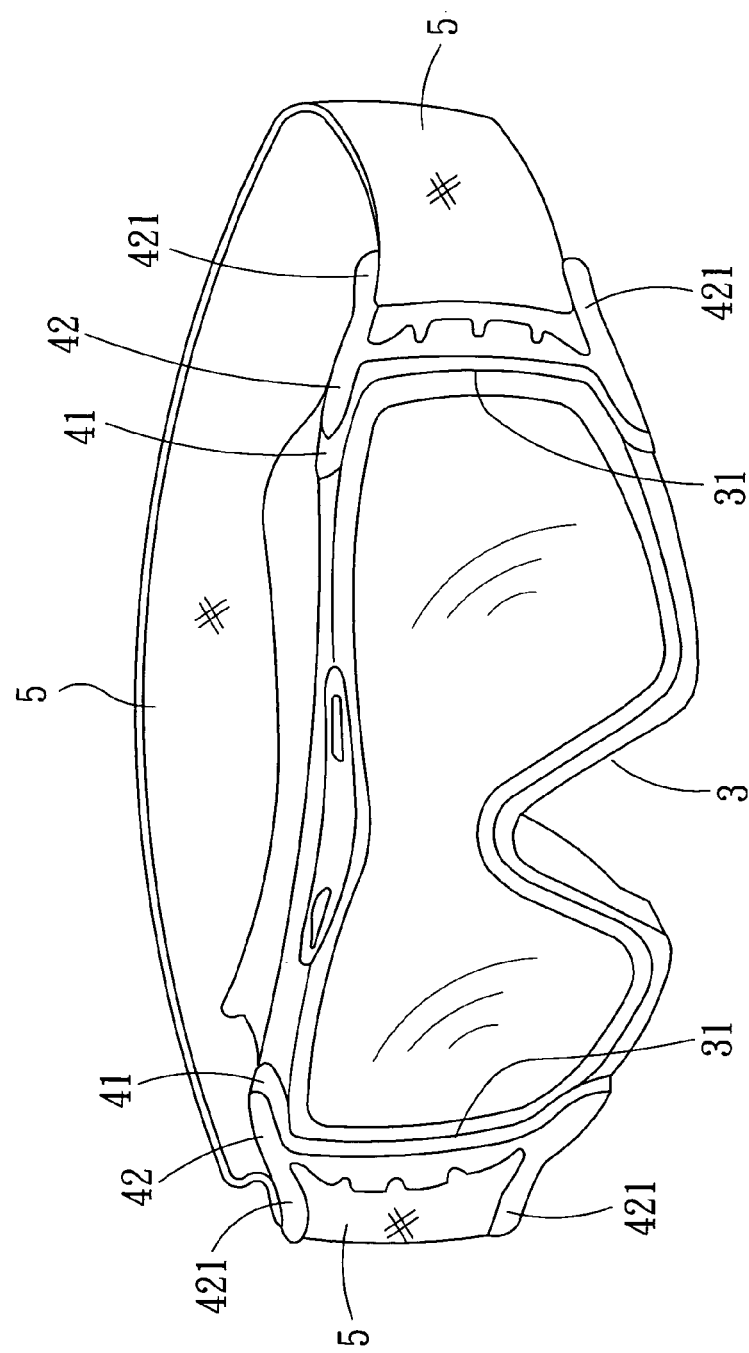
FIG. 3 is an elevational diagram of the present invention.
Figure 4:
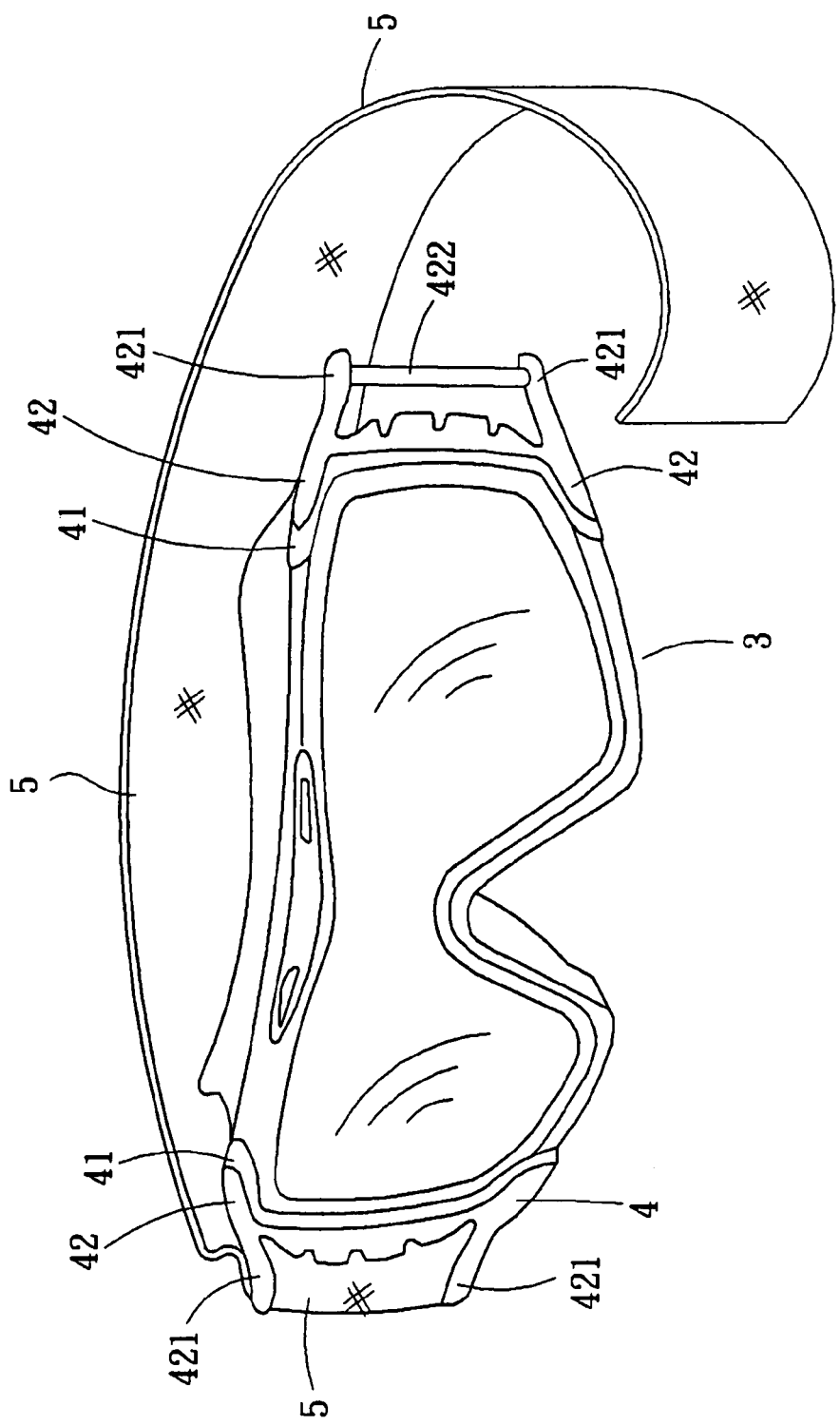
FIG. 4 is an exploded diagram of the present invention.
Figure 5:
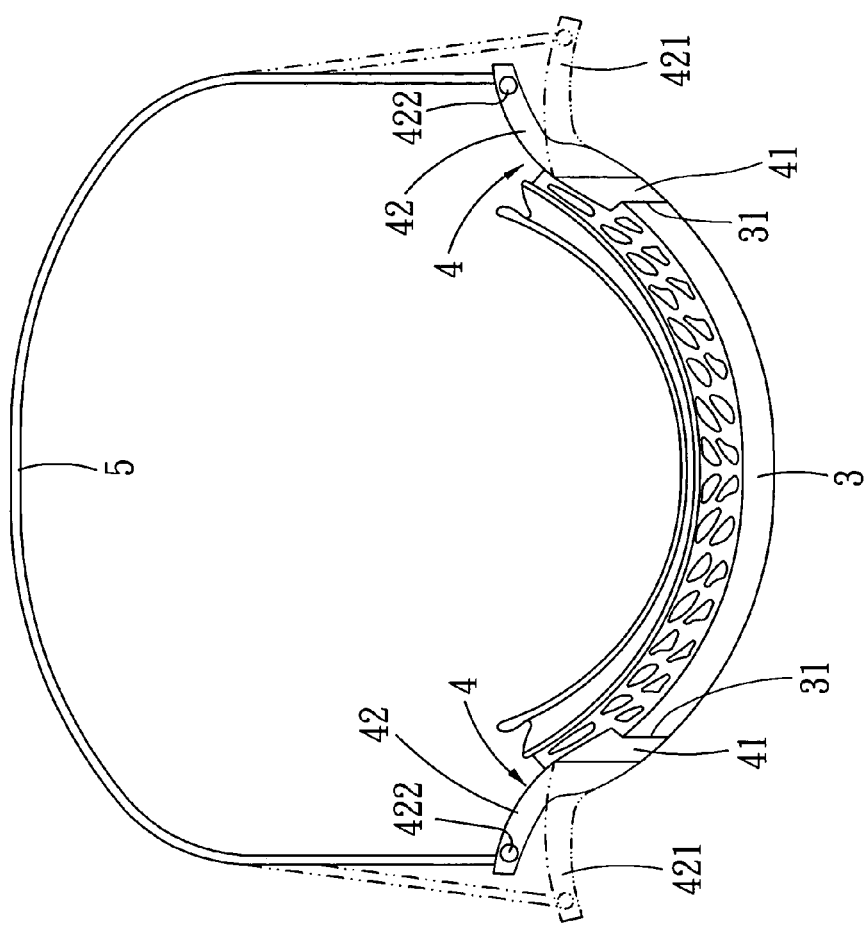
FIG. 5 is a top view of the present invention.

Referring to FIGS. 3 through 5, a preferred embodiment of a device to aid in shifting a pair of goggles of the present invention is shown. The device comprises two belt-connecting units 4 attached to two lateral edges 31 of a goggles frame 3, respectively. Each of the belt-connecting units 4 is composed of a rigid member 41 and a flexible member 42, which are made of different materials and abutted to each other. The rigid members 41 are attached to the respective lateral edges 31 of the goggles frame 3. Each of the flexible members 42 has an elastic linkage part 421 extending therefrom for connection with an elastic belt 5. Accordingly, before the outward movement of the goggles worn on the user's head, the elastic linkage part 421 can be bent outwardly and deformably, as indicated by dash lines in FIG. 5, so as to keep the elastic belt 5 from tightly fastening the both sides of user's head for easing off the contraction force. Moreover, the rigid members 41 are made of a rigid material, such as metal, hard plastic material and so on, while the flexible members 42 are made of an elastic, deformable plastic material.

Referring again to FIGS. 3 through 5, each of the elastic linkage parts 421 is a U-shaped member having two opposite inner surfaces connected to a rod 422 such that when the goggles frame 3 is swayed upwardly to be sleeved onto a headgear or helmet, the elastic belt 5 can be shifted outwardly in advance by the outwardly shifted elastic linkage parts 421 to prevent the elastic belt 5 from scraping or pulling the hair or skin. As a result, the present invention can overcome the discomfort occurred in the conventional structure completely. Moreover, the rods 422 are also made of a rigid material so that they can bear the pull force that outwardly shifts the elastic linkage part 421 without any deformation.

Referring again to FIGS. 3 through 5, the process of sleeving the goggles frame 3 onto the headgear or helmet is more effort-saving since the pull force can be applied to each rod 422 so as to allow the rod 422 and the elastic linkage part 421 to jointly form a torque (the torque is calculated by multiplying the force by the moment arm).

On the basis of the description mentioned above, the present invention indeed satisfies the requirements for patentability since it provides practicability and has never been published or used publicly. Therefore, it is submitted for a patent.

With the invention thus explained, it is apparent that various modifications and variations can be made without departing from the scope of the invention. It is therefore intended that this invention be limited only as indicated in the appended claims.

The invention claimed is:

1. A device to aid in shifting a pair of goggles comprising:
two belt-connecting units attached respectively to two lateral edges of a goggles frame of said pair of goggles, each of said belt-connecting units comprising an abutted rigid member and a flexible member, which are made of different materials, said rigid members being attached respectively to said two lateral edges of said goggles frame, and each of said flexible members having an elastic linkage part extending therefrom for connection with an elastic belt of said pair of goggles, whereby said elastic linkage parts are flexibly deformable so as to provide convenience and comfort in shifting said pair of goggles worn on a user's head; wherein each of said elastic linkage parts is a U-shaped member having two opposite inner surfaces connected to a rod.

2. A device to aid in shifting a pair of goggles of claim 1, wherein said rigid members are made of a metal material, and said flexible members are made of an elastic, deformable plastic material.

3. A device to aid in shifting a pair of goggles of claim 1, wherein said rigid members are made of a hard plastic material, and said flexible members are made of an elastic, deformable plastic material.

* * * * *